(12) United States Patent
Kassiou et al.

(10) Patent No.: US 11,414,459 B2
(45) Date of Patent: Aug. 16, 2022

(54) METABOLITE INSPIRED SELECTIVE OXYTOCIN RECEPTOR AGONISTS

(71) Applicant: Kinoxis Therapeutics Pty Ltd, Camberwell (AU)

(72) Inventors: Michael Kassiou, New South Wales (AU); Damien Gulliver, New South Wales (AU); Tristan Reekie, New South Wales (AU); Timothy Katte, New South Wales (AU); William Jorgensen, New South Wales (AU); Eryn Werry, New South Wales (AU)

(73) Assignee: Kinoxis Therapeutics Pty Ltd, Camberwell (AU)

( * ) Notice: Subject to any disclaimer, the term of this patent is extended or adjusted under 35 U.S.C. 154(b) by 0 days.

(21) Appl. No.: 16/650,943

(22) PCT Filed: Sep. 27, 2018

(86) PCT No.: PCT/AU2018/051062
§ 371 (c)(1),
(2) Date: Mar. 26, 2020

(87) PCT Pub. No.: WO2019/060962
PCT Pub. Date: Apr. 4, 2019

(65) Prior Publication Data
US 2020/0255475 A1 Aug. 13, 2020

(30) Foreign Application Priority Data
Sep. 28, 2017 (AU) .................. 2017903935

(51) Int. Cl.
*A61K 38/00* (2006.01)
*C07K 7/16* (2006.01)
*A61P 25/18* (2006.01)
*A61P 25/30* (2006.01)
*A61P 25/22* (2006.01)

(52) U.S. Cl.
CPC ............. *C07K 7/16* (2013.01); *A61P 25/30* (2018.01); *A61K 38/00* (2013.01)

(58) Field of Classification Search
CPC .......... A61K 38/00; A61P 25/18; A61P 25/22; A61P 25/30; C07K 7/16
See application file for complete search history.

(56) References Cited

U.S. PATENT DOCUMENTS

2016/0377635 A1* 12/2016 Martin, Jr. ............. G01N 1/405
436/86

FOREIGN PATENT DOCUMENTS

| WO | WO 2000/018424 A1 | 4/2000 |
| WO | WO 2002/067974 A1 | 9/2002 |
| WO | WO 2011/035330 A2 | 3/2011 |
| WO | WO 2015/185467 A1 | 12/2015 |

OTHER PUBLICATIONS

Lebl, M., "Observation of a conformational effect in peptide molecule by reverse-phase high-performance liquid chromatography", Journal of Chromatography, 1993, vol. 644, No. 2, p. 285-287.
Sciabola, S., et al., "Systematic N-methylation of oxytocin: Impact on pharmacology and intramolecular hydrogen bonding network", Bioorganic & Medicinal Chemistry, 2016, vol. 24, No. 16, p. 3513-3520.

* cited by examiner

*Primary Examiner* — Julie Ha
(74) *Attorney, Agent, or Firm* — Cooley LLP; Matthew Pavao

(57) ABSTRACT

The present disclosure relates to compounds of Formula I being cyclic metabolites of oxytocin. These derivatives have enhanced selectivity for the oxytocin receptor.

6 Claims, No Drawings

METABOLITE INSPIRED SELECTIVE OXYTOCIN RECEPTOR AGONISTS

CROSS-REFERENCE TO RELATED APPLICATIONS

This application is a U.S. National Phase Application, filed under 35 USC § 371, of International Application No. PCT/AU2018/051062, filed on Sep. 27, 2018, which claims priority to, and the benefit of, Australian Application No. 2017903935, filed on Sep. 28, 2017. The contents of each of these applications is herein incorporated by reference in their entirety.

FIELD OF THE INVENTION

The present disclosure relates to compounds, pharmaceutical compositions and methods for the treatment of a patient using metabolite inspired selective oxytocin receptor agonists.

BACKGROUND OF THE INVENTION

According to the World Health Organisation (WHO), 1 in 5 individuals have a diagnosable mental, neurological or developmental disorder. Almost 50% of the population will have a diagnosable mental disorder at some point in their life and at least half of these people will develop this condition prior to the age of 14. Whilst the manifestation of depression/anxiety dominate global incidence statistics, social anxiety disorder (SAD), also known as social phobia, is frequently co-morbid and often precedes the onset of these psychiatric disorders. Social withdrawal is a prominent feature of childhood developmental disorders such as autism and fragile X syndrome. As such, pharmacotherapies associated with promoting social function is of paramount importance. Additionally, several disorders have social withdrawal as a secondary symptom. Examples here include schizophrenia, major depressive disorder (MDD) and substance use disorders. Currently prescribed therapeutics (SSRIs and SNRIs) usually prescribed for MDD, have at best limited efficacy, slow onset of action, poor compliance and vast side effect profiles.

Evidence presented over the past 3 decades has identified the oxytocin (OT) receptor (OXTR) as a viable therapeutic target for pharmacological intervention. In rodent models, i.c.v. administration of OT promotes social behaviour whilst OT knock-out mice manifest social deficits. Furthermore, OT positively modulates a wide variety of social interactions including maternal behaviour, courtship, sexual behaviour and peer-to-peer interaction.

Results of human studies, in which OT is usually administered intranasally, show that OT can increase trust and co-operation, improve social memory and decrease social fear.2 Moreover, recent clinical trials indicated that administration of OT to a person with autism and social anxiety can restore some aspects of social functioning. The OT receptor therefore has immense potential for drug discovery aimed at alleviating serious psychiatric disorders. However, it is unlikely that intranasal OT will be an optimal therapeutic modality. Unfortunately, OT is a non-selective peptide capable of activating the arginine vasopressin receptors (V1a and V2) which have diverse peripheral roles. V1a receptors are located on vascular smooth muscle cells as well as cardio myocytes and modulate heart rate and blood pressure whilst the well-known anti-diuretic effects of vasopressin are modulated by V2 receptors located upon the kidneys. Furthermore, OT itself shows poor penetration of the blood brain barrier, negligible oral bioavailability and a short half-life upon peripheral administration. Due to these issues, clinical studies employing intranasal oxytocin have yielded only modest benefits in clinical populations.

The aforementioned disorders are among the most prevalent diseases and are some of the largest contributors to global burden of disease. A recent study by the Centre for Disease Control (USA) estimates the prevalence of autism among 8 year olds to be 1 in 110. SAD is the second most prevalent anxiety disorder, with the NIH estimating some 6.8% of American adults suffer from the disorder.

According to the WHO, schizophrenia affects some 24 million people worldwide and has one of the highest levels of chronicity of any disease. The WHO also estimate that alcohol abuse contributed to over 3 million deaths worldwide in the year 2012 (5.9% of all deaths). In the developed world, psychoactive substance abuse accounts for 33.4% of total years of life lost (DALYs) for males.

The idea to specifically target the neural substrates of social behaviour represents a paradigm shift from existing therapies for the above disorders.

For example, the use of antipsychotics in ASD (e.g. risperidone) is aimed at inhibiting aggressive and challenging behaviours rather than stimulating prosocial behaviours. The use of antidepressants in SAD (e.g. paroxetine, venlafaxine) assumes that low mood and generalised anxiety are primary drivers of social withdrawal in SAD and seeks to indirectly influence social anxiety through improving mood and decreasing global anxiety. Treatment of schizophrenia with antipsychotics (e.g. olanzapine, aripiprazole) seeks to control positive symptoms and to a certain extent neurocognitive impairment, but does not directly tackle the pervasive social withdrawal seen in the chronic disease state.

Current treatments for addictions provide either a substitute version of the abused drug (e.g. methadone, buprenorphine or varenicline) to control craving, or a therapeutic that may decrease craving through largely unknown mechanisms (e.g. acamprosate, naltrexone, baclofen, ondansetron). These current pharmacotherapies for addiction have limited efficacy at best, and none are aimed at the debilitating social dysfunction caused by these diseases. Although there are several psychological therapies for these disorders, their success is also limited.

In view of the above, it is desirable to provide compounds that address at least one of the aforementioned shortcomings of the prior art.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In one aspect of the invention, there is provided a compound of Formula I:

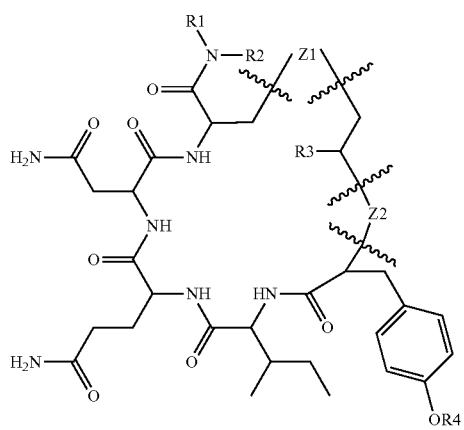

Formula I wherein:

R1 and R2 are each independently selected from the group consisting of: a substituted or unsubstituted alkylamide, a substituted or unsubstituted aryl, a substituted or unsubstituted heterocyclyl, a substituted or unsubstituted alkyl, or a substituted or unsubstituted alkylaryl; alternatively, R1 and R2 together form a cyclic structure selected from the group consisting of: a substituted or unsubstituted aryl, a substituted or unsubstituted heterocyclyl, or a substituted or unsubstituted alkyl;

R3 is selected from the group consisting of: H or $NH_2$;

R4 is selected from the group consisting of: H and substituted or unsubstituted $C_1$-$C_4$ alkyl;

Z1 is a substituted or unsubstituted tether of 2 or 3 atoms in chain length, with at least one of the 2 or 3 atoms is selected from the group consisting of: S and Se; and Z2 is a peptide isostere.

In an embodiment, R1 and R2 together form a substituted pyrrolidinyl having a substituent selected from the group consisting of: $C(=O)NH_2$, $C(=O)NHC(CH_2CH(CH_3)_2)C(=O)NH_2$, and $C(=O)NHC(CH_2CH(CH_3)_2)C(=O)NHCH_2C(=O)NH_2$. Preferably, R1 and R2 together form a substituted pyrrolidinyl having a substituent selected from the group consisting of: $C(=O)NH_2$ or $C(=O)NHC(CH_2CH(CH_3)_2)C(=O)NH_2$.

In an embodiment, R1 and R2 are each independently selected from the group consisting of: $CH_2C_6H_4F$, $CH_2C(=O)NH_2$, $CH_2C(=O)NHC(CH_2CH(CH_3)_2)C(=O)NH_2$, and $CH_2C(=O)NHC(CH_2CH(CH_3)_2)C(=O)NHCH_2C(=O)NH_2$. Preferably, at least one of R1 and R2 is $CH_2C_6H_4F$, and the other of R1 and R2 is $CH_2C(=O)NH_2$, $CH_2C(=O)NHC(CH_2CH(CH_3)_2)C(=O)NH_2$, and $CH_2C(=O)NHC(CH_2CH(CH_3)_2)C(=O)NHCH_2C(=O)NH_2$. More preferably, at least one of R1 and R2 is $CH_2C_6H_4F$, and the other of R1 and R2 is $CH_2C(=O)NH_2$ or $CH_2C(=O)NHC(CH_2CH(CH_3)_2)C(=O)NH_2$.

In an embodiment, Z1 is selected from the group consisting of:

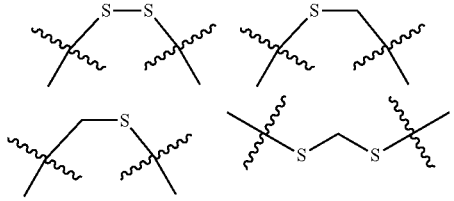

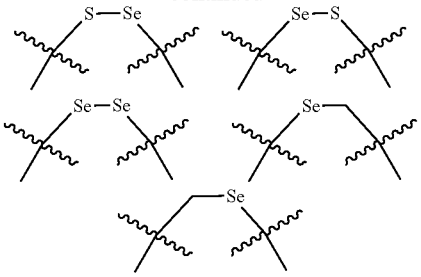

As discussed above, Z2 is a peptide isostere. A peptide isostere may also be referred to as a peptide bioisostere. For the avoidance of doubt, the peptide isostere is not an amide of the form $NHC(=O)$.

In an embodiment, Z2 is selected from the group consisting of: substituted or unsubstituted heterocyclyl, substituted or unsubstituted aryl; substituted or unsubstituted cycloalkyl; substituted or unsubstituted $C_2$-$C_3$ alkyl; substituted or unsubstituted $C_2$-$C_3$ alkenyl; substituted or unsubstituted $NHC_1$-$C_2$ alkyl; substituted or unsubstituted $NHC_2$ alkenyl; substituted or unsubstituted $OC_1$-$C_2$ alkyl; substituted or unsubstituted $OC_2$ alkenyl; substituted or unsubstituted $CH_2S(O)_n$; substituted or unsubstituted $NHS(O)_n$.

As used herein, the term "$C_1$-$C_3$ alkyl" either used alone or in compound terms refers to straight chain or branched saturated hydrocarbon groups, having 1 to 3 carbon atoms. Suitable alkyl groups include, but are not limited to: methyl, ethyl, propyl. The "$C_1$-$C_3$ alkyl" may be optionally substituted with one or more substituents. The substituents may replace one or more hydrogen atoms on any carbon atom or carbon atoms in the "$C_1$-$C_3$ alkyl" carbon atom chain.

As used herein, the term "$C_2$-$C_3$ alkenyl" either used alone or in compound terms refers to straight chain or branched unsaturated hydrocarbon groups, having 2 to 3 carbon atoms and including at least one carbon to carbon double bond. Suitable alkenyl groups include, but are not limited to: ethenyl or propenyl. The carbon to carbon double bond may be between any two adjacent carbon atoms. The "$C_2$-$C_3$ alkenyl" may be optionally substituted with one or more substituents. The substituents may replace one or more hydrogen atoms on any carbon atom or carbon atoms in the "$C_2$-$C_3$ alkenyl" carbon atom chain.

As used herein, the term "heterocyclyl" or "heterocyclic group" is intended to refer to an organic cyclic functional group that has at least one non-carbon atom as a member of its ring(s). The heterocyclic group may be a fused or unfused, saturated or unsaturated ring system. Examples of suitable heterocyclic groups include fused or unfused 3-, 4-, 5-, 6-, or 7-membered heterocyclic groups having one or more hetero ring atoms selected from N, O, or S.

In an embodiment, Z2 is selected from the group consisting of:

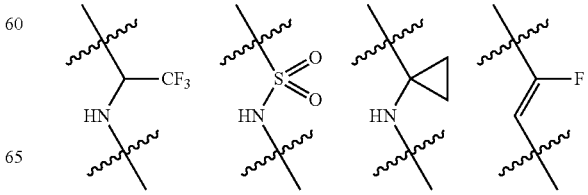

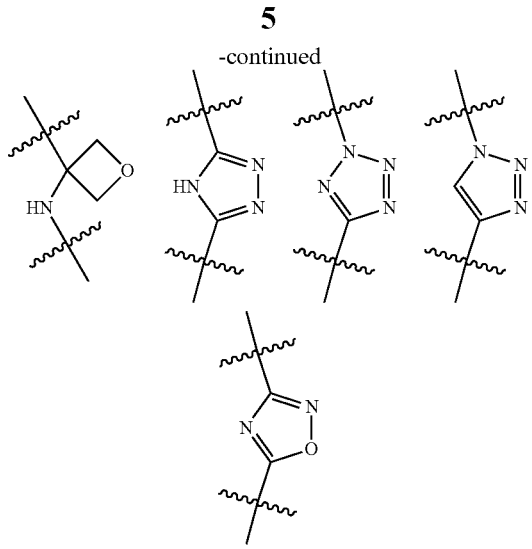

In an embodiment, each R1, R2, R3, R4, Z1, or Z2 that is substituted is independently substituted with one or more substituents selected from the group consisting of: F, Cl, Br, I, $NH_2$, $N=O$, $NO_2$, $NHCH_3$, OH, $OCH_3$, $OC\equiv N$, $ON=O$, SH, $SCH_3$, $S(=O)_nOH$, $S(=O)_nCH_3$, $SC\equiv N$, COOH, $CH_3$, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, $OCH_mBr_{(3-m)}$, 3 to 6-membered cycloalkyl, 3 to 6-membered heterocyclyl, or a 3 to 6-membered aryl; wherein n is an integer selected from the group consisting of: 0, 1, or 2; and wherein m is an integer selected from the group consisting of: 0, 1, or 2.

In another aspect of the invention, there is provided a pharmaceutical composition, the pharmaceutical composition comprising, consisting essentially of, or consisting of: a pharmaceutically acceptable compound of Formula I and a pharmaceutically acceptable carrier, diluent, or excipient, wherein:

R1 and R2 together form a substituted pyrrolidinyl having a substituent selected from the group consisting of: $C(=O)NH_2$, or $C(=O)NHC(CH_2CH(CH_3)_2)C(=O)NH_2$; or alternatively at least one of R1 and R2 is selected from the group consisting of: $CH_2C(=O)NH_2$, or $CH_2C(=O)NHC(CH_2C(CH_3)_2H)C(=O)NH_2$;

R3 is selected from the group consisting of: H or $NH_2$;

R4 is selected from the group consisting of: H and substituted or unsubstituted $C_1$-$C_4$ alkyl;

Z1 is a substituted or unsubstituted tether of 2 or 3 atoms in chain length, with at least one of the 2 or 3 atoms is selected from the group consisting of: S and Se;

Z2 is an amide bond or a peptide isostere.

In an embodiment, where at least one of R1 and R2 is selected from the group consisting of: $CH_2C(=O)NH_2$, or $CH_2C(=O)NHC(CH_2C(CH_3)_2H)C(=O)NH_2$; the other of R1 and R2 is $CH_2C_6H_4F$.

In an embodiment, Z1 is selected from the group consisting of:

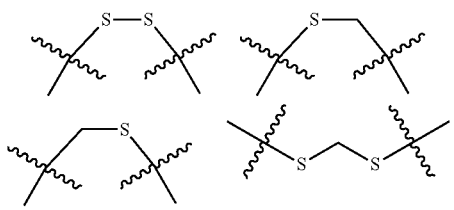

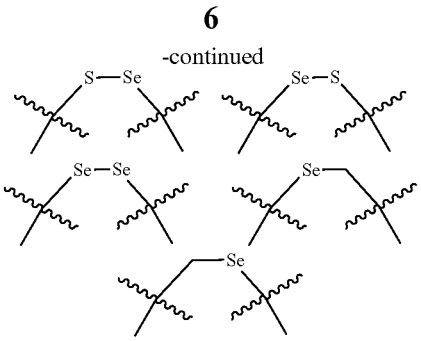

In an embodiment, Z2 is selected from the group consisting of: substituted or unsubstituted heterocyclyl, substituted or unsubstituted aryl; substituted or unsubstituted cycloalkyl; substituted or unsubstituted $C_2$-$C_3$ alkyl; substituted or unsubstituted $C_2$-$C_3$ alkenyl; substituted or unsubstituted $NHC_1$-$C_2$ alkyl; substituted or unsubstituted $NHC_2$ alkenyl; substituted or unsubstituted $OC_1$-$C_2$ alkyl; substituted or unsubstituted $OC_2$ alkenyl; substituted or unsubstituted $CH_2S(O)_n$; substituted or unsubstituted $NHS(O)_n$.

In an embodiment, Z2 is selected from the group consisting of:

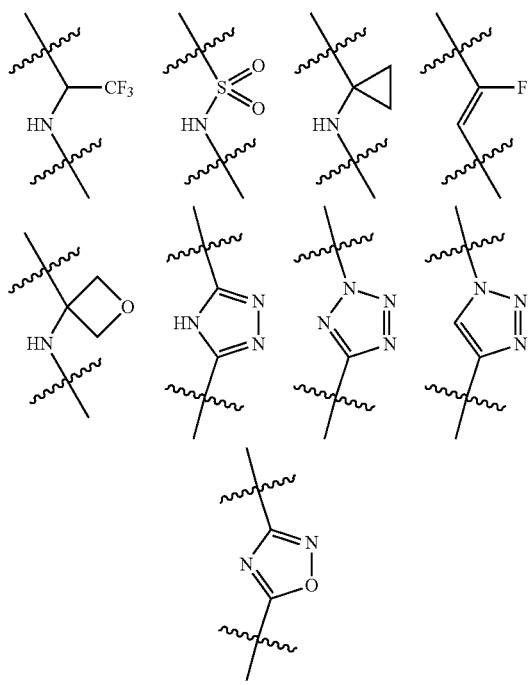

In an embodiment, each R1, R2, R3, R4, Z1, or Z2 that is substituted is independently substituted with one or more substituents selected from the group consisting of: F, Cl, Br, I, $NH_2$, $N=O$, $NO_2$, $NHCH_3$, OH, $OCH_3$, $OC\equiv N$, $ON=O$, $=O$, SH, $SCH_3$, $S(=O)_nOH$, $S(=O)_nCH_3$, $SC\equiv N$, COOH, $CH_3$, $CH_mF_{(3-m)}$, $CH_mCl_{(3-m)}$, $CH_mBr_{(3-m)}$, $OCH_3$, $OCH_mF_{(3-m)}$, $OCH_mCl_{(3-m)}$, $OCH_mBr_{(3-m)}$, 3 to 6-membered cycloalkyl, 3 to 6-membered heterocyclyl, or a 3 to 6-membered aryl; wherein n is an integer selected from the group consisting of: 0, 1, or 2; and wherein m is an integer selected from the group consisting of: 0, 1, or 2.

In a third aspect of the invention, there is provided a method comprising: administering a compound or a pharmaceutical composition as previously defined to a subject.

In an embodiment, the method comprises administering the compound or pharmaceutical composition to the subject in an amount effective to treat or prevent a condition in a subject.

In an embodiment, the method comprises administering the compound or pharmaceutical composition to a subject that suffers from, or is recovering from a substance abuse disorder; or a subject that is recovering from the substance abuse disorder and seeks to maintain ongoing abstinence from the substance.

In a fifth aspect of the invention, there is provided the use of a compound or a pharmaceutical composition as defined previously in the manufacture of a medicament for the therapeutic treatment or prevention of a condition in a subject and/or maintaining ongoing abstinence from a substance in the subject.

In a sixth aspect of the invention there is provided a compound or a pharmaceutical composition for treating or preventing a condition in a subject, or for maintaining ongoing abstinence from a substance in the subject. Preferably, there is provided a compound or a pharmaceutical composition when used to treat or prevent a condition in a subject, or to maintain ongoing abstinence from a substance in the subject.

The condition may be a social dysfunction, such as social withdrawal, aggressiveness, an anti-social disorder, or an addiction to a substance. The condition may be a psychiatric disorder, such as an autistic spectrum disorder, a social anxiety disorder, a depressive disorder including major depressive disorder, or schizophrenia. The substance may be, for example, alcohol, cocaine, opiates, amphetamines, heroin, and nicotine.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

The present invention is based on the discovery of oxytocin and cyclic metabolites thereof are useful in treating a range of mental, neurological, and behavioural disorders. In particular, oxytocin and cyclic metabolites thereof have been found to act as selective agonists for the oxytocin receptor (OXTR). Furthermore, the inventors have found that these cyclic metabolites of oxytocin have enhanced selectivity and efficacy when compared with oxytocin. Accordingly, in one form, the invention relates to: pharmaceutical compositions comprising these cyclic oxytocin metabolites, methods of treatment using these cyclic oxytocin metabolites, and preparation of pharmaceutical compounds containing these cyclic oxytocin metabolites. The inventors are of the view that this increase in selectivity and/or efficacy should similarly apply to structurally related cyclic metabolites of compounds including: merotocin, demoxytocin, and carbetocin.

Oxytocin (OT) is a peptide of nine amino acids with the sequence cysteine-tyrosine-isoleucine-glutamine-asparagine-cysteine-proline-leucine-glycine-amide (Cys-Tyr-Ile-Gln-Asn-Cys-Pro-Leu-Gly-$NH_2$). The C-terminus of the peptide has been converted to a primary amide and a disulfide bridge joins the cysteine moieties resulting in the cyclic structure. Cyclic metabolites of oxytocin include Cys-Tyr-Ile-Gln-Asn-Cys-Pro-Leu-N $H_2$, Cys-Tyr-Ile-Gln-Asn-Cys-Pro-N $H_2$, and Cys-Tyr-Ile-Gln-Asn-Cys-$NH_2$, wherein a disulfide bridge joins the cysteine moieties. Interestingly, OT and the cyclic metabolites thereof undergo different metabolic pathways within the central nervous system (CNS) as compared with peripheral metabolism. Notably, inhibition of OT metabolism within the CNS prevents some of the behavioural characteristics observed following intracerebroventricular administration which is suggestive that the metabolites of OT have uncharacterised behavioural roles.

Surprisingly, the inventors have found that cyclic oxytocin metabolites not only act as OXTR agonists, but in many instances are highly selective for the OXTR, having minimal or no affinity for V1aR. These oxytocin metabolites are comparatively small molecules (when compared with oxytocin), and are also less susceptible to issues of bioavailability and metabolic breakdown that plague some of these larger molecules.

However, as with oxytocin, these cyclic metabolites may still undergo peripheral metabolism and/or intracranial metabolism. Both of these forms of metabolism can result in decyclisation of the ring structure and the formation of linear analogues that have little to no selectivity or efficacy.

By way of background, once in the central nervous system, cleavage of the amide bond between the Cys and Tyr in cyclic compounds including oxytocin, merotocin, demoxytocin, carbetocin, and cyclic metabolites thereof can occur as a result of intracranial metabolism. In each case, cleaving this bond opens the cyclic ring structure to form a linear analogue. In the case of oxytocin and cyclic metabolites thereof, these linear analogues exhibit reduced or no selectivity and/or efficacy. Stabilisation of the cyclic structure can be achieved by substituting a peptide isostere that is resilient to intracranial metabolism in place of the amide bond between the Cys and Tyr. This prevents intracranial metabolism of the amide bond between Cys-Tyr, and prevents decyclisation of the compounds. Thus, in certain forms, the invention relates to compounds including: oxytocin, merotocin, demoxytocin, carbetocin, and cyclic metabolites thereof in which the amide bond between the Cys and Tyr has been substituted with a peptide isostere.

As noted above, during peripheral metabolism, the disulfide bridge of the compound is cleaved thus opening the ring structure and forming a linear analogue. These linear analogues do not exhibit the selectivity and/or efficacy demonstrated by oxytocin, and cyclic oxytocin metabolites. Thus, in certain forms of the invention (for example where compounds of the invention are administered in a manner that peripheral metabolism can occur), stabilisation of this bridge is desirable. Stabilisation of this bridge may be achieved by substitution of the disulfide bridge with a suitable isostere that is resilient to peripheral metabolism. Another way to avoid peripheral metabolism is to administer the compound directly to the central nervous system, or via a route that avoids peripheral metabolism.

In view of the above, the invention also relates to a pharmaceutical composition including the compound of Formula I. The compound of Formula I is included in a pharmaceutically effective amount, sufficient to produce a desired effect upon a process or condition of a disease.

An appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. The amount of a compound of the present invention in the composition will also depend upon the particular compound in the composition.

The pharmaceutical composition may further comprise other therapeutically active compounds which are usually applied in the treatment of the disclosed disorders or conditions. Selection of the appropriate agents for use in combination therapy may be made by one of ordinary skill in the art, according to conventional pharmaceutical principles. The combination of therapeutic agents may act synergistically to effect the treatment or prevention of the various disorders or conditions disclosed herein. Using this approach, one may be able to achieve therapeutic efficacy with lower dosages of each agent, thus reducing the potential for adverse side effects.

Compounds and compositions of the invention may be formulated for any appropriate route of administration including, for example, topical (for example, transdermal or ocular), oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. Within yet other embodiments, compositions provided herein may be formulated as a lyophilizate.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydroxypropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or arachis oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan mono-oleate, and condensation products of partial esters derived from fatty acids and hexitol with ethylene oxide such as polyoxyethylene sorbitan mono-oleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

Compositions of the invention may be formulated for local or topical administration, such as for topical application to the skin. Formulations for topical administration typically comprise a topical vehicle combined with active agent(s), with or without additional optional components.

Suitable topical vehicles and additional components are well known in the art, and it will be apparent that the choice of a vehicle will depend on the particular physical form and mode of delivery. Topical vehicles include organic solvents such as alcohols (for example, ethanol, iso-propyl alcohol or glycerine), glycols such as butylene, isoprene or propylene glycol, aliphatic alcohols such as lanolin, mixtures of water and organic solvents and mixtures of organic solvents such as alcohol and glycerine, lipid-based materials such as fatty acids, acylglycerols including oils such as mineral oil, and fats of natural or synthetic origin, phosphoglycerides, sphingolipids and waxes, protein-based materials such as collagen and gelatine, silicone-based materials (both non-volatile and volatile), and hydrocarbon-based materials such as microsponges and polymer matrices.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form. Solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity. Both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels, and often do not contain emulsifiers. Liquid topical products often contain solvents, emulsifiers, moisturizers, emollients, fragrances, dyes/colorants, preservatives and other active ingredients that increase or enhance the efficacy of the final product.

Emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminium silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Typical modes of delivery for topical compositions include application using the fingers, application using a physical applicator such as a cloth, tissue, swab, stick or brush, spraying including mist, aerosol or foam spraying, dropper application, sprinkling, soaking, and rinsing. Controlled release vehicles can also be used, and compositions may be formulated for transdermal administration (for example, as a transdermal patch).

Pharmaceutical compositions may be formulated as sustained release formulations such as a capsule that creates a slow release of modulator following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of modulator release. The amount of modulator contained within a sustained release formulation depends upon, for example, the site of implantation, the rate and expected duration of release and the nature of the disorder to be treated or prevented.

In another form, the invention relates to a method of treating a subject, the method including administering a pharmaceutically effective amount of a compound of Formula I, in a pharmaceutically acceptable form, to the subject.

As used herein, a "subject" refers to an animal, such as a mammalian or an avian species, including a human, an ape, a horse, a cow, a sheep, a goat, a dog, a cat, a guinea pig, a rat, a mouse, a chicken etc.

The inventors have found that compounds of Formula I are particularly useful for the treatment of a range of neurological conditions or disorders. The condition or disorder may be a social dysfunction, such as social withdrawal, aggressiveness, an anti-social disorder, or an addiction to a substance (for example, alcohol, cocaine, opiates, amphetamines, heroin, and nicotine). The condition or disorder may be a psychiatric disorder, a social anxiety disorder, a depressive disorder including major depressive disorder, memory loss, or schizophrenia, or a developmental disorder such as an autistic spectrum disorder. The condition or disorder may be a stress disorders including post-traumatic stress disorder.

As used herein, the terms "treating" and "treatment" may include one or more of, ameliorating a symptom of a disorder in a subject, blocking or ameliorating a recurrence of a symptom of a condition or disorder in a subject, and decreasing in severity and/or frequency a symptom of a condition or disorder in a subject.

In another aspect the present invention provides a kit or article of manufacture including a compound of Formula I or pharmaceutical composition including a compound of Formula I as described herein.

In other embodiments there is provided a kit for use in a therapeutic or prophylactic application mentioned herein, the kit including: a container holding a compound of Formula I or pharmaceutical composition including a compound of Formula I; and a label or package insert with instructions for use.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a compound of Formula I or composition which is effective for treating the condition and may have a sterile access port (for example the container may be an intravenous solution bag or a vial having a stopper pierceable by a hypodermic injection needle). The label or package insert indicates that the dendrimer or composition is used for treating a disorder. In one embodiment, the label or package insert includes instructions for use and indicates that the therapeutic or prophylactic composition can be used to treat a disorder described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat a disorder or prevent a complication stemming from a disorder described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the compound of Formula I or therapeutic or prophylactic pharmaceutical composition including a compound of Formula I. In one embodiment, the device is a syringe. The therapeutic or prophylactic composition may be provided in the device in a state that is ready for use or in a state requiring mixing or addition of further components.

It will be understood that the invention disclosed and defined in this specification extends to all alternative combinations of two or more of the individual features mentioned or evident from the text. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

EXAMPLES

Examples Demonstrating the Selectivity of the Compounds of Formula I

Peptide Synthesis

All peptides were synthesised using solid phase peptide synthesis with purity and identity determined by analytical reverse phase HPLC and mass spectrometry.

HPLC column was a 150×4.6 mm, Monitor C18 (Column Engineering). Solvent A (0.1% trifluoroacetic acid in 100% water). Solvent B (0.1% trifluoroacetic acid in 90% acetonitrile/aqueous). Gradient: 10% B for 1.0 min; 10-66.6% B (linear) over 15 min with a flow rate of 1.5 mL/min. Wavelength used for detection 214 nm.

Mass Spectrometer was a Perkin-Elmer Sciex API 100 ionspray instrument with ion counting detection. Eluent 0.1% acetic acid in 60% acetonitrile (aqueous).

Competition Radioligand Binding Assay Experimental Procedures

Binding affinity of truncated oxytocin derivatives was indexed by competitive displacement of [3H]-oxytocin or [3H]-vasopressin at Kd concentrations. Membranes (50 µg/well) from OT or V1a receptor-expressing HEK293 cells were incubated in a final volume of 200 µL containing [3H]-oxytocin (10 nM) or [3H]-vasopressin (2 nM) alongside competing compounds (0.1 nM-100 µM) in reaction buffer (50 mM Tris-HCl, 5 mM $MgCl_2$, pH 7.4). Reactions were incubated for 90 min at 4 C to reach equilibrium, and terminated by rapid filtration over glass fibre filters (Whatman GF/A 1.6 µM), and washing with ice-cold reaction buffer. Radioactivity was detected after soaking filters in Microscint 0 using a Microbeta2 2450 microplate-reader (Perkin Elmer). Nonspecific binding was determined in the presence of 1 μM cold oxytocin or vasopressin (Sigma-Aldrich), respectively.

HTRF-IP1 Accumulation Assay Experimental Procedures

OT or V1a receptor-expressing HEK293 cells were seeded onto clear, poly-L-lysine (100 μg/mL)-coated 384 well plates at a density of $8.75 \times 10^3$ cells per well. Levels of receptor activation induced by compounds were assessed at concentrations ranging from 1 nM to 100 μM using the HTRF IP-One kit (CisBio International, Bagnolssur-Cze, France), according to manufacturers protocol. For agonist assessment, cells were incubated with compounds for 1 h prior to the addition of Ab-Cryptate and IP1-d2. The ligand concentration that induced a 50% maximal response (EC50) was used to evaluate functional effects across compounds. For antagonist assessment, cells were pre-incubated with test compounds (1 nM-100 μM) solubilized in stimulation buffer for 30 min prior to the addition of an EC70 concentration of oxytocin or vasopressin mixed with compounds or DMSO control (0.1%). Cells were then incubated for a further 1 h, and Ab-Cryptate and IP1-d2 added. The ligand concentration that inhibited 50% of oxytocin or vasopressin-induced response (IC50) was used to evaluate antagonistic functional effects across compounds.

Results

The receptor binding and functional efficacy of oxytocin (OT) and the primary central nervous system (CNS) metabolites of OT are shown below in Table 1. These data shows the selective activation of OXTR over V1aR.

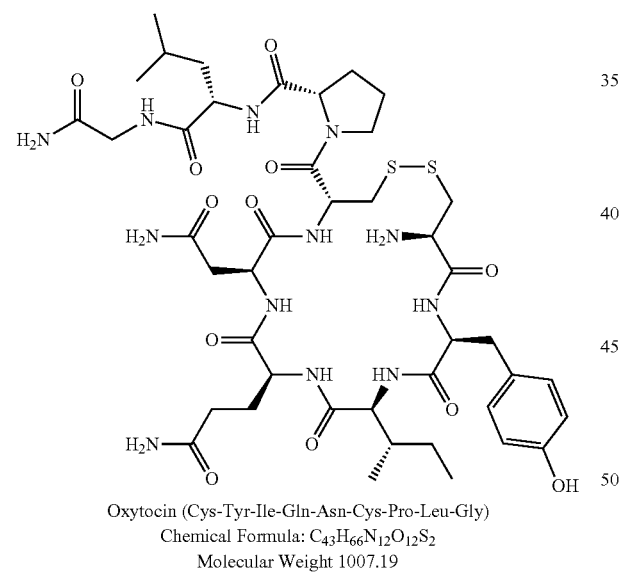

Oxytocin (Cys-Tyr-Ile-Gln-Asn-Cys-Pro-Leu-Gly)
Chemical Formula: $C_{43}H_{66}N_{12}O_{12}S_2$
Molecular Weight 1007.19

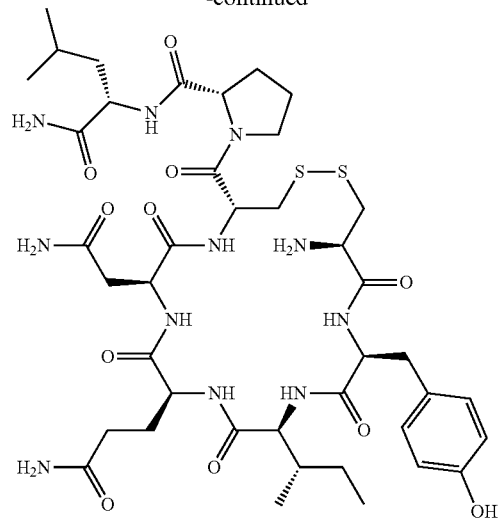

Oxytocin Metabolite A (Cys-Tyr-Ile-Gln-Asn-Cys-Pro-Leu)
Chemical Formula: $C_{41}H_{63}N_{11}O_{11}S_2$,
Molecular Weight 950.14, Purity 99.65%.

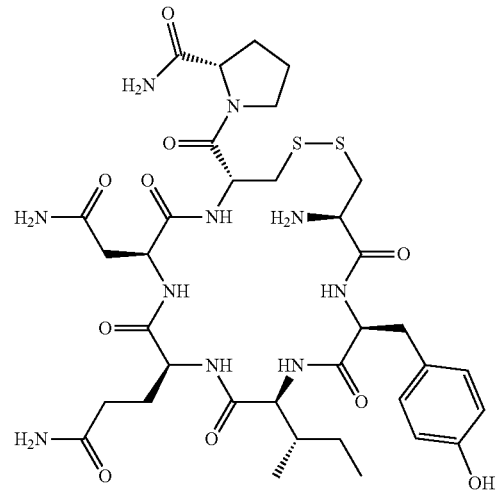

Oxytocin Metabolite B (Cys-Tyr-Ile-Gln-Asn-Cys-Pro)
Chemical Formula: $C_{35}H_{52}N_{10}O_{10}S_2$,
Molecular Weight 836.98, Purity 98.03%.

TABLE 1

Receptor binding and functional efficacy of oxytocin (OT) and the primary central nervous system (CNS) metabolites of OT (Metabolites A and B)

| Peptide | OXTR $K_i$ (nM) | $V_{1a}R$ $K_i$ (nM) | OXTR $EC_{50}$ | Emax (% OXT) | $V_{1a}R$ $EC_{50}$ | $E_{max}$ (% AVP) | OXTR $IC_{50}$ | $V_{1a}R$ $IC_{50}$ |
|---|---|---|---|---|---|---|---|---|
| Oxytocin | 10.8 | 105.9 | 35.7 | 100 | 109.1 | 82 | >10,000 | >10,000 |
| Metabolite A | 138.2 | 748.6 | 273.6 | 79.2 | >10,000 | n/a | >10,000 | >10,000 |
| Metabolite B | 72.6 | 104.5 | 110.5 | 74.1 | >10,000 | n/a | >10,000 | >10,000 |

The reverse peptide sequence for oxytocin has also been tested and observed to exhibit activity at the OXTR or V1aR receptors. This applies to the reverse sequence of both metabolite A and B.

While oxytocin metabolites A and B exhibit enhanced selectivity and activity when compared with oxytocin, these metabolites are subject to cleavage of the Cys-Tyr amide bond as a result of intracranial metabolism. Cleavage of the Cys-Tyr amide bond results in the internal ring structure being opened and the formation of linear analogue compounds. As a comparative study, a number of linear analogue compounds were synthesised and tested. In all cases, cleavage of the Cys-Tyr bond resulted in a loss in selectivity and/or activity. The linear analogue compounds that were tested are illustrated below:

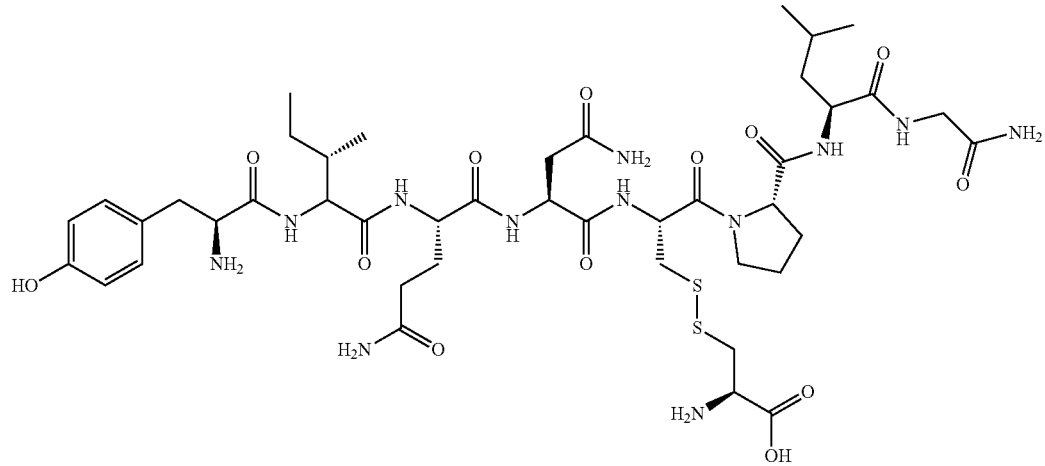

Tyr-Ile-Gln-Asn-Cys(Cys)-Pro-Leu-Gly
Retention time = 7.36 min, Purity 98.54%,
Mass spectrum = 1025.1 Dalton

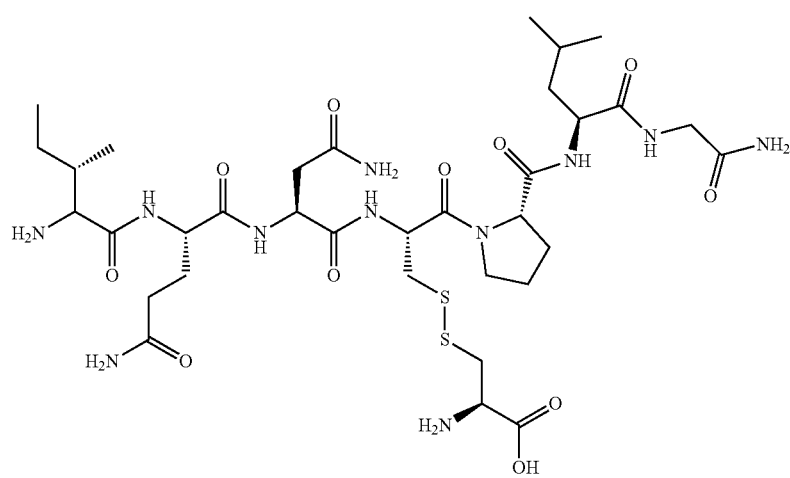

Ile-Gln-Asn-Cys(Cys)-Pro-Leu-Gly
Retention time = 6.37 min, Purity 97.79%,
Mass spectrum = 862.0 Dalton -continued
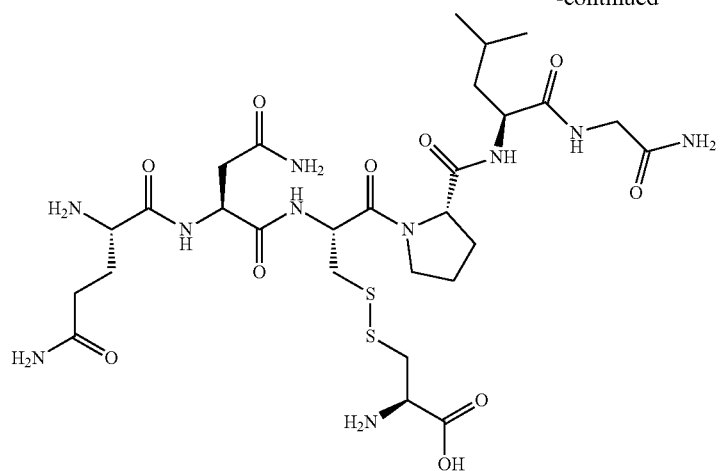
Gln-Asn-Cys(Cys)-Pro-Leu-Gly
Retention time = 5.92 min, Purity 94.84%,
Mass spectrum = 749.4 Dalton
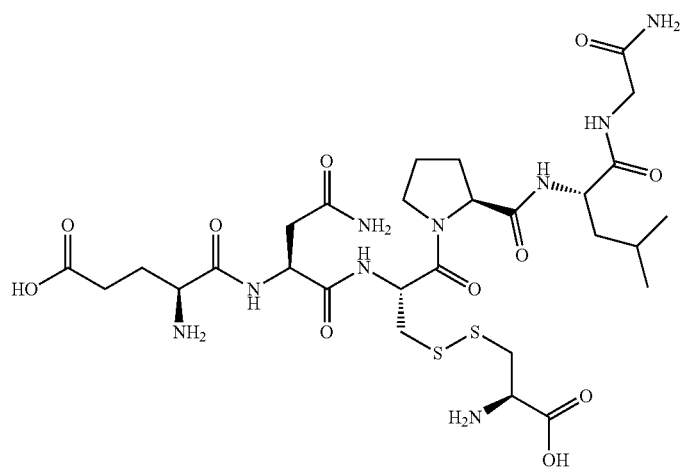
Glu-Asn-Cys(Cys)-Pro-Leu-Gly
Retention time = 5.92 min, Purity 95.10%,
Mass spectrum = 750.4 Dalton
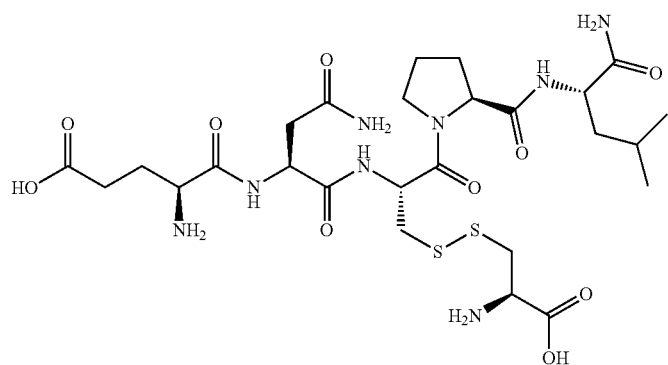
Glu-Asn-Cys(Cys)-Pro-Leu
Retention time = 5.86 min, Purity 96.03%,
Mass spectrum = 692.8 Dalton -continued

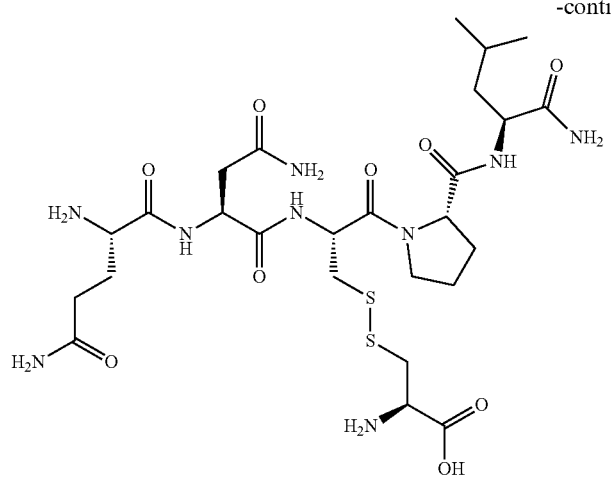

Gln-Asn-Cys(Cys)-Pro-Leu
Retention time = 5.83 min, Purity 95.01%,
Mass spectrum = 692.5 Dalton

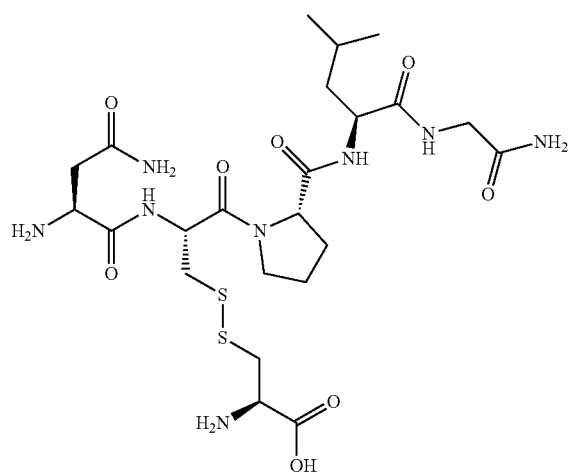

Asn-Cys(Cys)-Pro-Leu-Gly
Retention time = 5.59 min, Purity 97.52%,
Mass spectrum = 692.8 Dalton

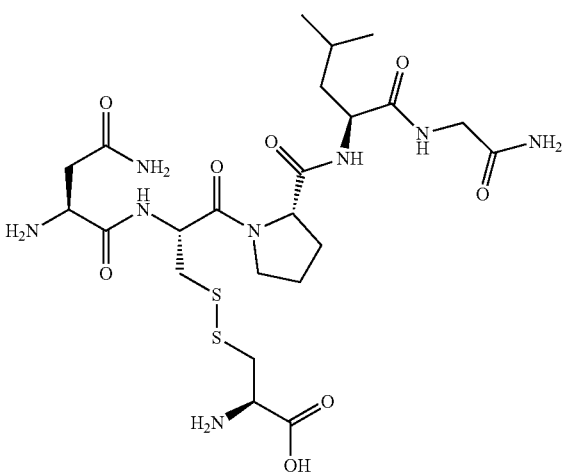

Asn-Cys(Cys)-Pro-Leu
Retention time = 5.64 min, Purity 98.79%,
Mass spectrum = 564.3 Dalton In view of the increased selectivity and efficacy of metabolites of Oxytocin, the inventors are of the view that the below metabolites of merotocin, demoxytocin, carbetocin may similarly exhibit enhanced selectivity and efficacy over merotocin, demoxytocin, and carbetocin respectively. Merotocin, demoxytocin, carbetocin, and the respective metabolites are also subject to cleavage of the Cys-Tyr amide bond as a result of intracranial metabolism. Stabilisation of this amide bond with a peptide isostere that cannot be metabolised within the brain will thus avoid conversion of these compounds to a respective linear compound via ring opening due to metabolic cleavage of the Cys-Tyr amide bond. This should similarly allow these compounds to maintain their activity within the brain.

Merotocin Metabolite A
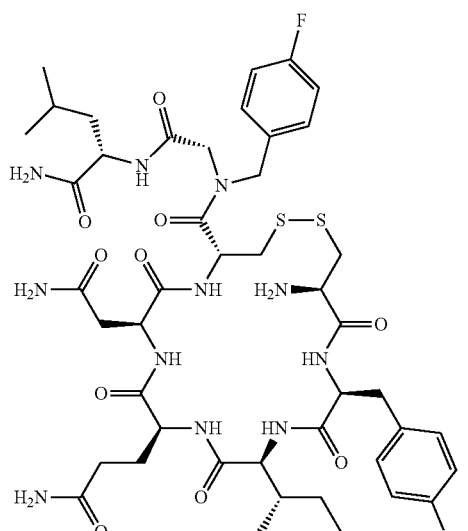
Chemical Formula: C$_{46}$H$_{66}$FN$_{11}$O$_{11}$S
Molecular Weight: 1000.16
Demoxytocin Metabolite A
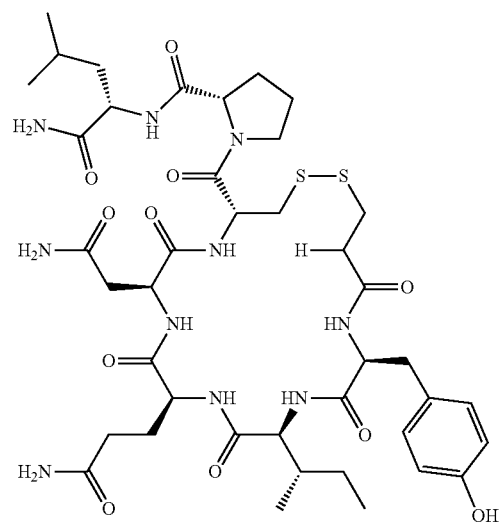
Chemical Formula: C$_{41}$H$_{62}$N$_{10}$O$_{11}$S$_2$
Molecular Weight: 935.13
Merotocin Metabolite B
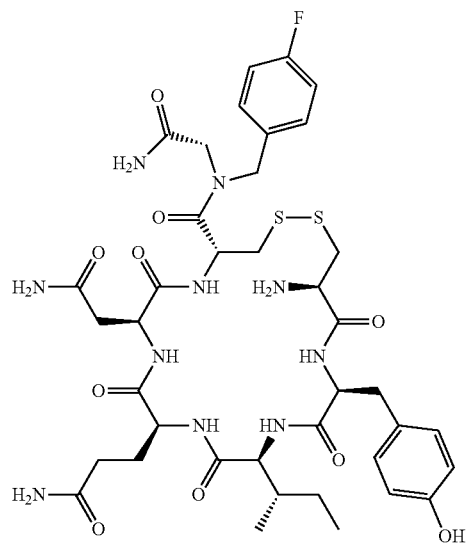
Chemical Formula: C$_{40}$H$_{55}$FN$_{10}$O$_{10}$S
Molecular Weight: 887.00
Demoxytocin Metabolite B
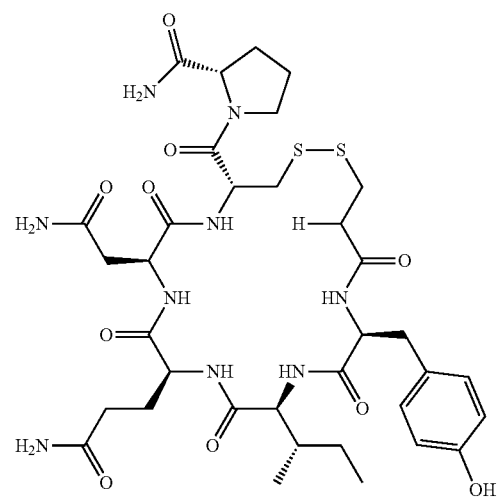
Chemical Formula: C$_{35}$H$_{51}$N$_9$O$_{10}$S$_2$
Molecular Weight: 821.97

-continued

Carbetocin Metabolite A

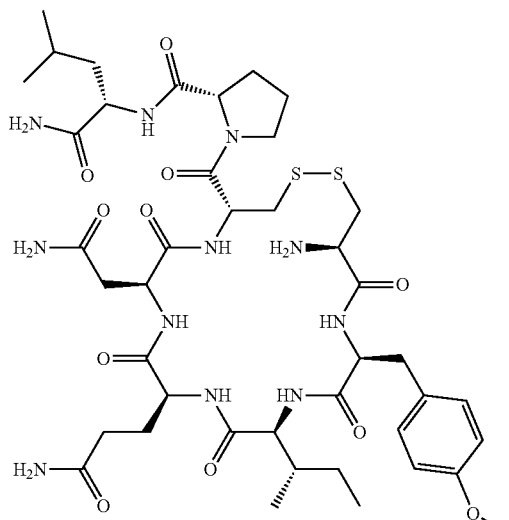

Chemical Formula: $C_{43}H_{67}N_{11}O_{11}S$
Molecular Weight: 946.14

Carbetocin Metabolite B

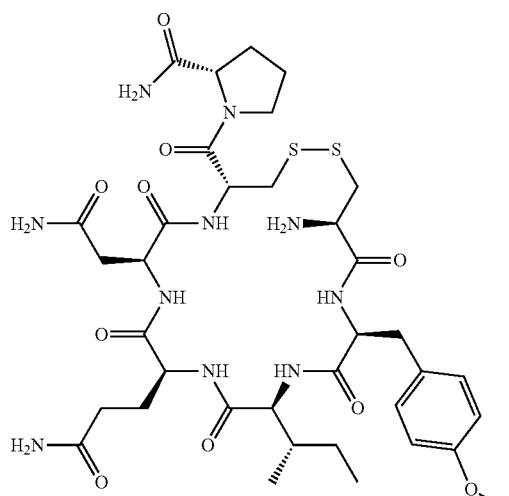

Chemical Formula: $C_{37}H_{56}N_{10}O_{10}S$
Molecular Weight: 832.98

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A pharmaceutical composition comprising a compound of Formula I and a pharmaceutically acceptable carrier, diluent, or excipient:

Formula I

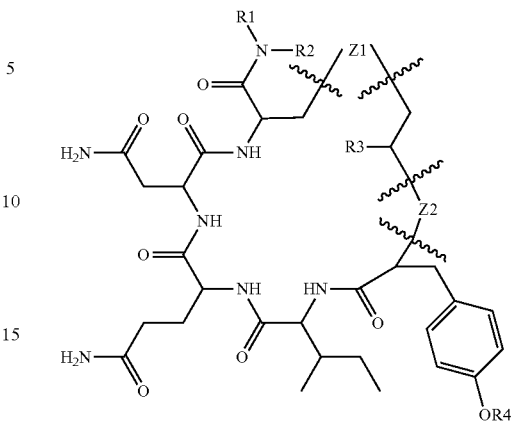

wherein: R1 and R2 together form a substituted pyrrolidinyl having a substituent selected from the group consisting of: $C(=O)NH_2$, and $C(=O)NHCH(CH_2CH(CH_3)_2)C(=O)NH_2$; or alternatively at least one of R1 and R2 is selected from the group consisting of: $CH_2C(=O)NH_2$, and $CH_2C(=O)NHCH(CH_2CH(CH_3)_2)C(=O)NH_2$, and the other being $CH_2C_6H_4F$;

R3 is selected from the group consisting of: H and $NH_2$;

R4 is selected from the group consisting of: H and substituted or unsubstituted $C_1$-$C_4$ alkyl;

Z1 is a substituted or unsubstituted tether of 2 or 3 atoms in chain length, with at least one of the 2 or 3 atoms is selected from the group consisting of: S and Se;

Z2 is selected from the group consisting of:

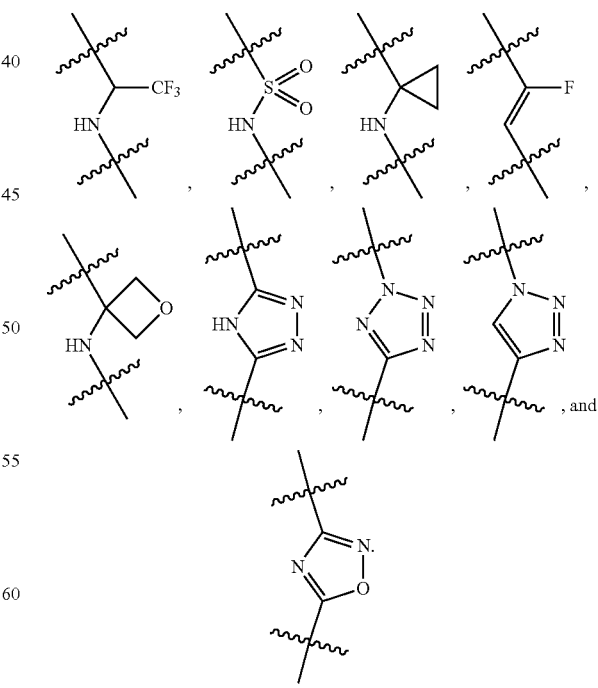

2. The pharmaceutical composition of claim 1, wherein Z1 is selected from the group consisting of:

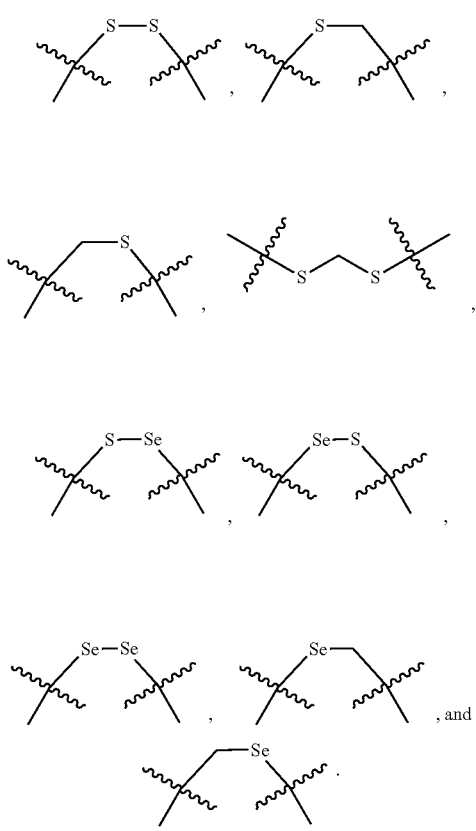

3. The pharmaceutical composition of claim 1, wherein when at least one of R1 and R2 is selected from the group consisting of: $CH_2C(=O)NH_2$, and $CH_2C(=O)NHCH(CH_2CH(CH_3)_2)C(=O)NH_2$; the other of R1 and R2 is $CH_2C_6H_4F$.

4. A pharmaceutical composition comprising a pharmaceutically acceptable carrier, diluent, or excipient and a compound selected from the group consisting of:

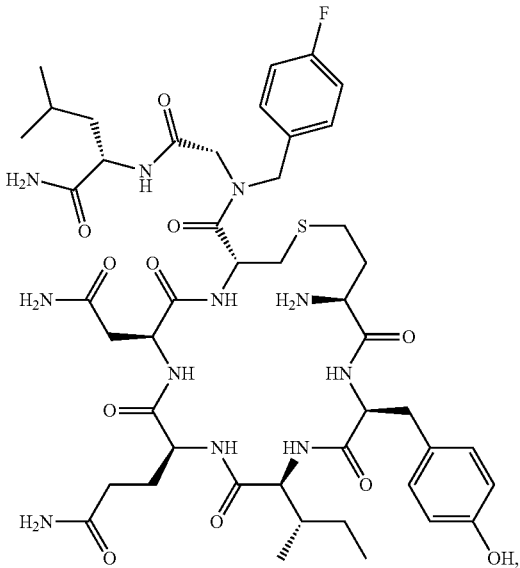

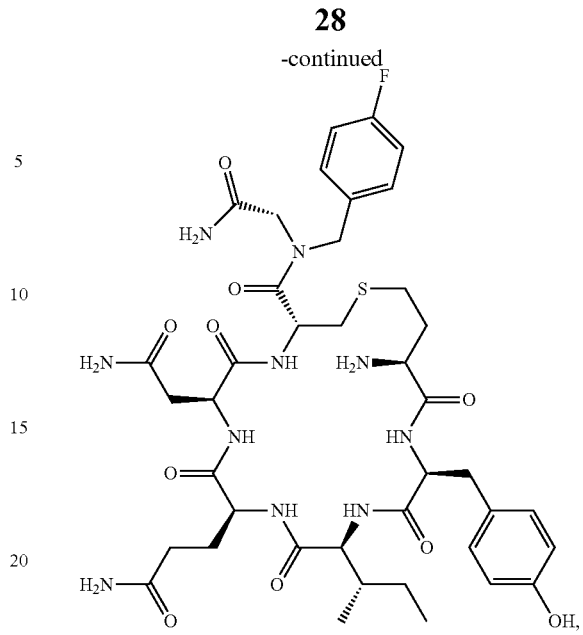

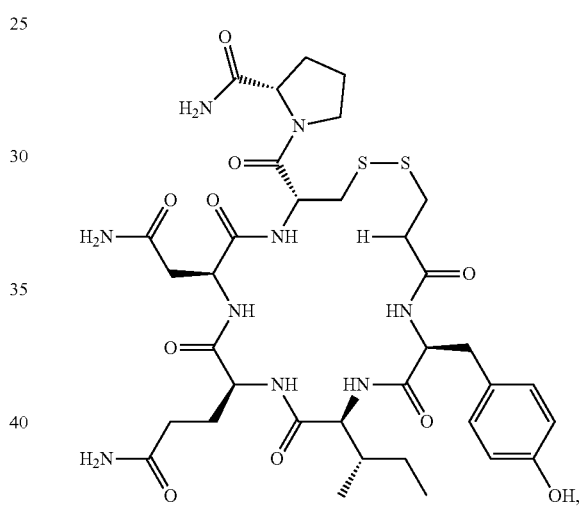

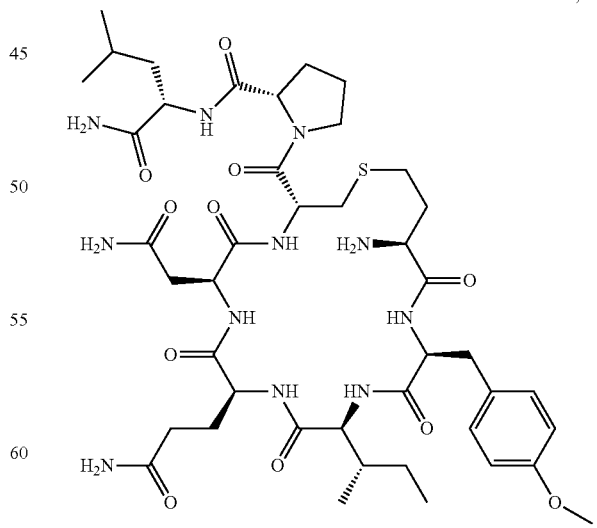

5. A method of treating a social dysfunction, a psychiatric disorder, or a substance abuse disorder, the method comprising:

administering an effective amount of a pharmaceutical composition according to claim 1 to a subject in need thereof.

6. The method of claim 5, wherein the subject suffers from, or is recovering from, a substance abuse disorder; or the subject is recovering from the substance abuse disorder and seeks to maintain ongoing abstinence from the substance.

\* \* \* \* \*